United States Patent
Ryan et al.

[19]

[11] Patent Number: 6,042,581
[45] Date of Patent: *Mar. 28, 2000

[54] TRANSVASCULAR TMR DEVICE AND METHOD

[75] Inventors: Timothy J. Ryan, Portola Valley, Calif.; Thomas J. Fogarty, 3274 Alpine Rd., Portola Valley, Calif. 94028

[73] Assignee: Thomas J. Fogarty, Portola Valley, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/745,869

[22] Filed: Nov. 8, 1996

[51] Int. Cl.[7] ...................................................... A61B 17/39
[52] U.S. Cl. ............................... 606/45; 604/114; 607/101
[58] Field of Search .............................. 600/381; 607/99, 607/122; 606/41, 45, 49, 7, 15

[56] References Cited

U.S. PATENT DOCUMENTS

| | | |
|---|---|---|
| 4,774,949 | 10/1988 | Fogarty . |
| 4,990,134 | 2/1991 | Auth . |
| 5,041,109 | 8/1991 | Abela . |
| 5,093,877 | 3/1992 | Aita . |
| 5,287,861 | 2/1994 | Wilk ......................................... 128/898 |
| 5,323,781 | 6/1994 | Ideker et al. ............................. 607/122 |
| 5,348,554 | 9/1994 | Imran et al. ............................... 606/41 |
| 5,366,490 | 11/1994 | Edwards et al. ........................... 607/99 |
| 5,380,316 | 1/1995 | Aita . |
| 5,409,019 | 4/1995 | Wilk . |
| 5,429,144 | 7/1995 | Wilk . |
| 5,536,247 | 7/1996 | Thornton . |
| 5,573,533 | 11/1996 | Strul .......................................... 606/34 |
| 5,643,255 | 7/1997 | Organ ........................................ 606/41 |
| 5,697,882 | 12/1997 | Eggers et al. ............................ 604/114 |

OTHER PUBLICATIONS

Banai, et al., Angiogenic–Induced Enhancement of Collateral Blood Flow to Ischemic Myrocardium by Vascular Endothelial Growth Factor in Dogs, 5 Circulation 2183 (May 1994).

Sen, et al., Further Studies In Multiple Transmyocardial Acupuncture As A Method of Myocardial Revascularization, 64 Surgery 861 (1968).

Cooley, et al., Transmyocardial Laser Revascularization, 21 Texas Heart Inst. J. 230 (Nov. 3, 1994).

Wakabayashi, et al., Myocardial Boring for the Ischemic Heart, 95 Arch. Surg. 743 (Nov. 1967).

*Primary Examiner*—Linda C. M. Dvorak
*Assistant Examiner*—Roy Gibson
*Attorney, Agent, or Firm*—K. David Crockett, Esq.; Crockett & Crockett

[57] ABSTRACT

A catheter assembly for performing transmyocardial revascularization through the coronary arteries or veins, and a method of using this assembly for creating TMR channels through the myocardium coronary artery shunts through the myocardium.

2 Claims, 8 Drawing Sheets

TRANSVASCULAR TMR DEVICE AND METHOD

FIELD OF THE INVENTION

This invention relates to transmyocardial revascularization.

BACKGROUND OF THE INVENTION

Transmyocardial revascularization (TMR) is one of several surgical treatments for heart disease. Coronary bypass surgery, balloon angioplasty, and coronary stent placement are well known methods of providing increased blood flow to the heart after the acoronary arteries become restricted and occluded as a result of cardiovascular disease. These methods improve the blood supply to the heart. Transmyocardial revascularization takes another approach, and refers to the method of punching, lasing, burning, drilling or coring channels directly into the heart muscle itself, so that these channels may communicate with the intraventricular space. The channels created in TMR may extend across the entire thickness of the heart muscle, or myocardium. For reasons that are not entirely clear, creation of these channels has a clearly beneficial and therapeutic effect on the blood supply to the myocardium. While it is thought that the channels created by TMR permit blood to flow directly from the ventricles into the myocardium, and supply blood to the intramyocardial arteriolar/capillary network, it is not entirely clear that the channels created by TMR must persist and maintain patency (stay open) for a lasting therapeutic effect. It has been surmised that the act of creating the channels stimulates growth of new blood vessels and thus improves blood supply to the part of the heart that is affected by poor blood supply from the coronary arteries.

A variety of devices and methods of performing TMR have been used or attempted. An early use of TMR is discussed in Sen, et al., Further Studies In Acupuncture As A Method A Myocardial Revascularization, 64 Surgery 861 (1968). In this study, TMR was accomplished with biopsy needles, trephines and cannulas. The article discusses a number of other TMR studies, indicating good therapeutic effect at the time.

Aita, Method for Intra-Operative Myocardial Device Revascularization, U.S. Pat. No. 5,380,316 (Jan. 10, 1995) illustrates the use of a laser to burn or lase channels from the outside of the heart, through the myocardium and endocardium and into the endocardial space. The device is illustrated in use in the left ventricle. Aita provides a flexible catheter and a fiber optic waveguide which enables the laser to be applied to the exterior surfaces of the heart through an incision in the chest. In Aita's other work, Aita, Optical Fiber Lasing Apparatus, U.S. Pat. No. 5,093,877 (Mar. 3, 1992), he teaches that laser catheters used inside the arteries should be designed to avoid applying laser energy to the artery walls, and presents a design for a laser lens which purportedly greatly reduces possible perforation of the side wall of the artery. Likewise, Abela, Laser Apparatus For The Recanalization Of Vessels And The Treatment Of Other Cardiac Conditions, U.S. Pat. No. 5,041,109 presents a laser designed specifically to prevent perforation of the blood vessel during use of a laser catheter inside the blood vessel.

Cooley, et al., Transmyocardial Laser Revascularization, 21 Texas Heart Inst. J. 230 (Nov. 3, 1994) discusses the typical case of TMR in which the patient's chest is opened by thoracotomy to expose the heart to a laser. The laser is used to lase channels through the heart and into the left ventricle. The epicardial side of each channel is closed by clotting after hemostasis, or by suturing. In this procedure, the laser pulses were synchronized with the R wave of the patient's EKG, which corresponds to the contraction of the heart muscle. Later evaluation indicated beneficial effect in the treated area of the heart, and some patent channels apparently corresponding to the lased channels.

SUMMARY

The devices and methods presented below permit transmyocardial revascularization to be accomplished percutaneously, or more simply, from the coronary arteries or veins which surround the heart. One advantage of this approach is that is may be accomplished with instruments inserted through the vasculature, with access gained through a small incision in the thigh or neck, makes use of the existing vascular bed, i.e. the coronary arteries and veins, to avoid the necessity of entering the chest cavity via a highly invasive thoracotomy required by prior art techniques. Another advantage is that any residual bleeding caused by the revascularization bleeds into the coronary arteries rather than into the chest cavity or into the pericardial space.

A variety of new devices are used to accomplish the percutaneous transmyocardial revascularization. In one embodiment, mechanical boring devices are combined with deflecting catheters to create a catheter assembly capable of boring a channel sideways from any one of the coronary arteries or veins into the myocardium. In another embodiment, an end-firing laser is used in combination with the deflecting catheter to make a side channeling catheter assembly. Another embodiment comprises a side firing laser especially adapted via choice of laser and lens assembly to lase deep and narrow channels in the myocardium. Yet another embodiment uses an RF catheter to channel through the blood vessel wall and myocardium. For clarity, all these means of creating channels in the myocardium are referred to generally as channeling catheters, and the action they perform on the heart is referred to generally as channeling, but they may be more specifically referred to as punching, boring, tunneling, burning, ablating, lasing, vaporizing, cutting, cauterizing, etc., as the case may be.

Transmyocardial revascularization is accomplished with the devices enclosed. Also, other related procedures may be performed. For example, a coronary-myocardial-coronary shunt may be created, resulting in a bypass around an occluded portion of a coronary blood vessel where the bypass goes through the myocardium. A channel may be created from a coronary artery into the myocardium and terminating in the myocardium without communicating with the ventricular space or another major coronary blood vessel. Thus a variety of revascularization of shunting procedures may be accomplished with the devices disclosed below.

DETAILED DESCRIPTION OF THE INVENTION

Figure 1:
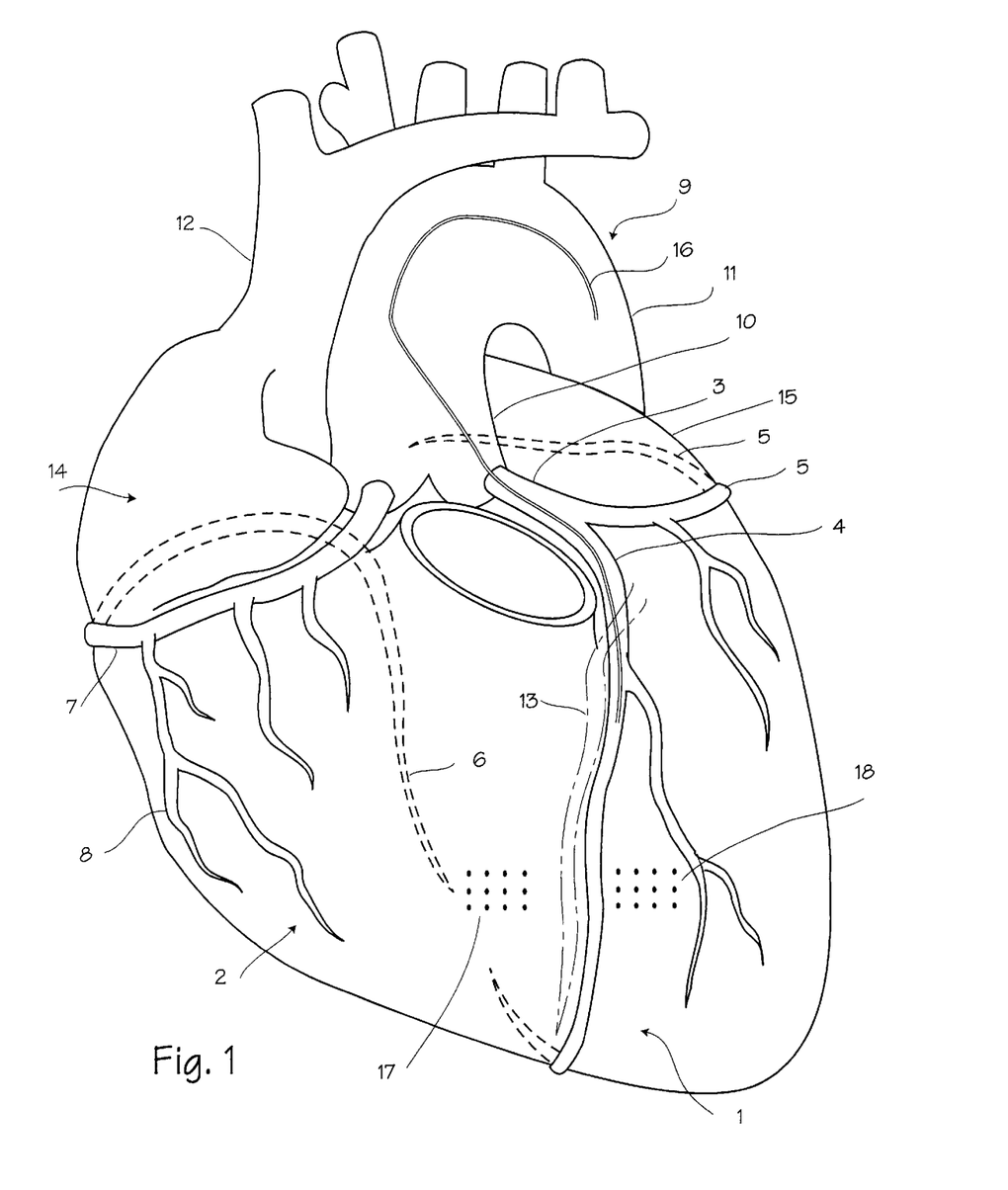
FIG. 1 is an anterior view of the heart showing the TMR catheter in its approach to the left ventricle.

FIG. 1 shows the human heart as viewed from the front. In medical terms, this is called the anterior view of the heart. In reference to the procedure described below, the significant structures include the left ventricle shown generally as item 1, the right ventricle 2, the left coronary artery 3 and the left anterior descending branch 4 of the left coronary artery (LAD), the circumflex artery 5 and the intraventricular branch artery 6 (both shown in phantom as they are located on the posterior surface of the heart), the right coronary artery 7 and the marginal branch 8 or the right coronary artery. The aorta 9, including the ascending aorta 10 and the descending aorta 11, provide catheter access to the coronary arteries as required in method of the invention which uses the coronary arteries to perform transpercutaneous TMR through the coronary arteries. The superior vena cava 12 provides access to the various coronary veins as required to perform the transpercutaneous TMR procedure through the veins surrounding the heart. Such veins as the great cardiac vein 13 and the posterior vein may be accessed through the vena cava. Other important structures of the heart are also shown, though they do not come into play in the description of the inventions set forth below. These structures include the right atrium 14 and the left atrium 15. The TMR channeling catheter 16 is shown in place to indicate the placement of new channels to be created by the channeling catheter. The catheter has been inserted into the distal LAD from the femoral artery in the groin of the patient, and this is accomplished by percutaneous insertion of the catheter into the femoral artery using the Seldinger technique, or with a cutdown of the femoral artery. The catheter is steered up the descending aorta 11, over the aortic arch and down the descending aorta 10, where it bends into the left coronary artery and LAD, to the distal portion of the LAD 4 which overlies the left ventricle 1 or the intraventricular septum. TMR may be accomplished through this route with the devices and methods described below. In contrast, the prior art method of accomplishing TMR is to expose the anterior and lateral surfaces of the heart and punch holes or lase holes from the exterior of the heart through the epicardium, and into and through the myocardium. The exterior locations of the TMR channels produced from the exterior of the heart in a typical TMR procedure indicated by the phantom matrices of holes are indicated at items 17 and 18.

Figures 2, 3, 4:
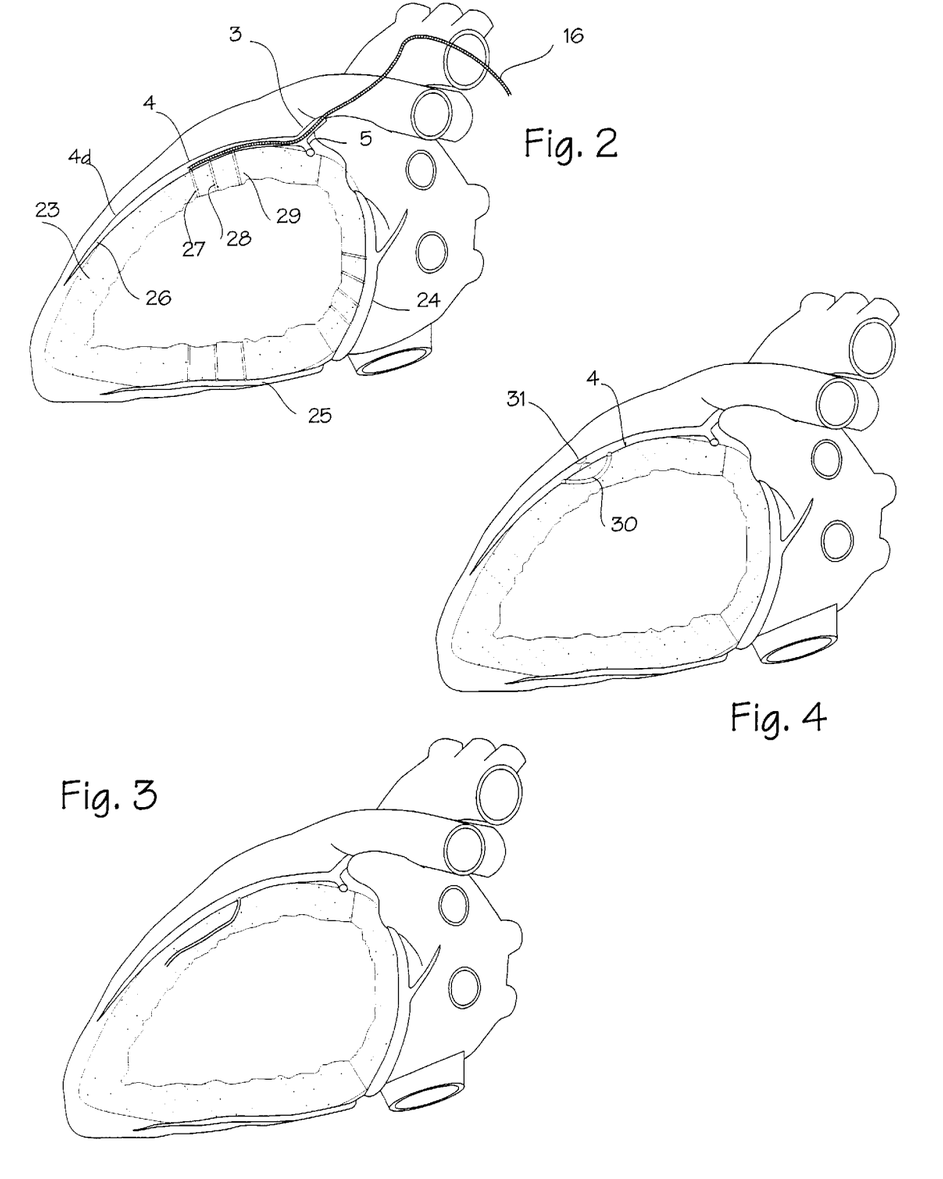
FIG. 2 is a lateral view of the heart in partial cross section, showing the TMR catheter in place in its approach to the left ventricle.
FIG. 3 is a lateral view of the heart in partial cross section illustrating a variation of the procedure.
FIG. 4 is a lateral view of the heart in partial cross section showing the arterio-myocardial shunt accomplished transpercutaneously.

FIG. 2 shows a lateral view of the human heart, as seen from the left side. The left coronary artery 3 and LAD artery 4 are prominent in this view, and run over the anterior wall 23 of the left ventricle. A short length of the left circumflex artery 5 is also seen in this view, leading to the posterior surface of the heart. A coronary vein 24 and the posterior descending right coronary artery 25 can also be seen in this view. The wall of the left ventricle is very thick, and is the strongest muscle of the heart. It is also the most susceptible is ischemia and infarct. For this reason, the inventions are described in reference to treatment of the left ventricle wall and the arteries that supply the left ventricle, although it should be recognized that the beneficial effect of the procedures and devices can be used in all areas of the heart. Thus, as seen in FIG. 2, the channeling catheter 16 extends into the distal portion 4d of the LAD 4. The channeling catheter, described in several embodiments below, is used to bore through the posterior wall 26 of the LAD, which is contiguous with the anterior surface of the left ventricle wall 23, and through the left ventricle wall into the chamber of the left ventricle. Other channels may be made from the coronary vein 24 and the descending branch of the right coronary artery 25 as illustrated.

The channels 27, 28 and 29 created in this fashion are similar in all respects to the channels created in open TMR procedures, except that the channels originate inside the arteries instead of originating on the surface of the heart. The channels may originate in the diseased and occluded portion of the artery (channel 27) or in a healthy and patent section (channels 28 and 29). It is expected that several such channels will be created in each transvascular TMR procedure. When the channeling catheter is removed, the LAD is left intact except for the small punctures or channel openings which will heal in time, or which may be treated to remain open and provide the added benefit of flow through the native vasculature after crossing the intramyocardial channels 27, 28, and 29 into the coronary artery.

The origin of the channel may close immediately after the procedure is accomplished, as is typical of open TMR procedures. However, immediate hemostasis in not required because any bleeding will flow into the coronary artery, rather than into the pericardial space, so that immediate closure of the point of entry is not essential. It is expected that several such channels will be created in each transvascular TMR procedure. When the channeling catheter is removed, the LAD is left intact except for the small punctures which will heal in time, and several presumably patent channels remain to provide the beneficial effect of the TMR procedure. In some instances, the origin of the channel may be treated to cause it to remain open. Blood may reach endangered myocardium directly through the newly created channel, or through new vessels which grow in response to the treatment. Blood may also reach threatened myocardium by flowing through the channel, then into the native coronary artery and subsequently to regions of the myocardium fed by the distal segment of the existing coronary artery.

Thus, in contrast to open TMR techniques which require immediate closure of the pericardial surface, and endocardial techniques which rely on careful control of the depth of the channel created from the endocardial surface or immediate sealing of any epicardial puncture, the methods and devices described here for transvascular TMR may be successfully employed without closing the origin or epicardial opening of the channels. Thus, the technique of transvascular TMR enables the surgeon to combine TMR channels with native blood vessels to take advantage of the pre-exiting native blood vessels to improve blood flow in areas remote from the TMR channels.

Figure 5:
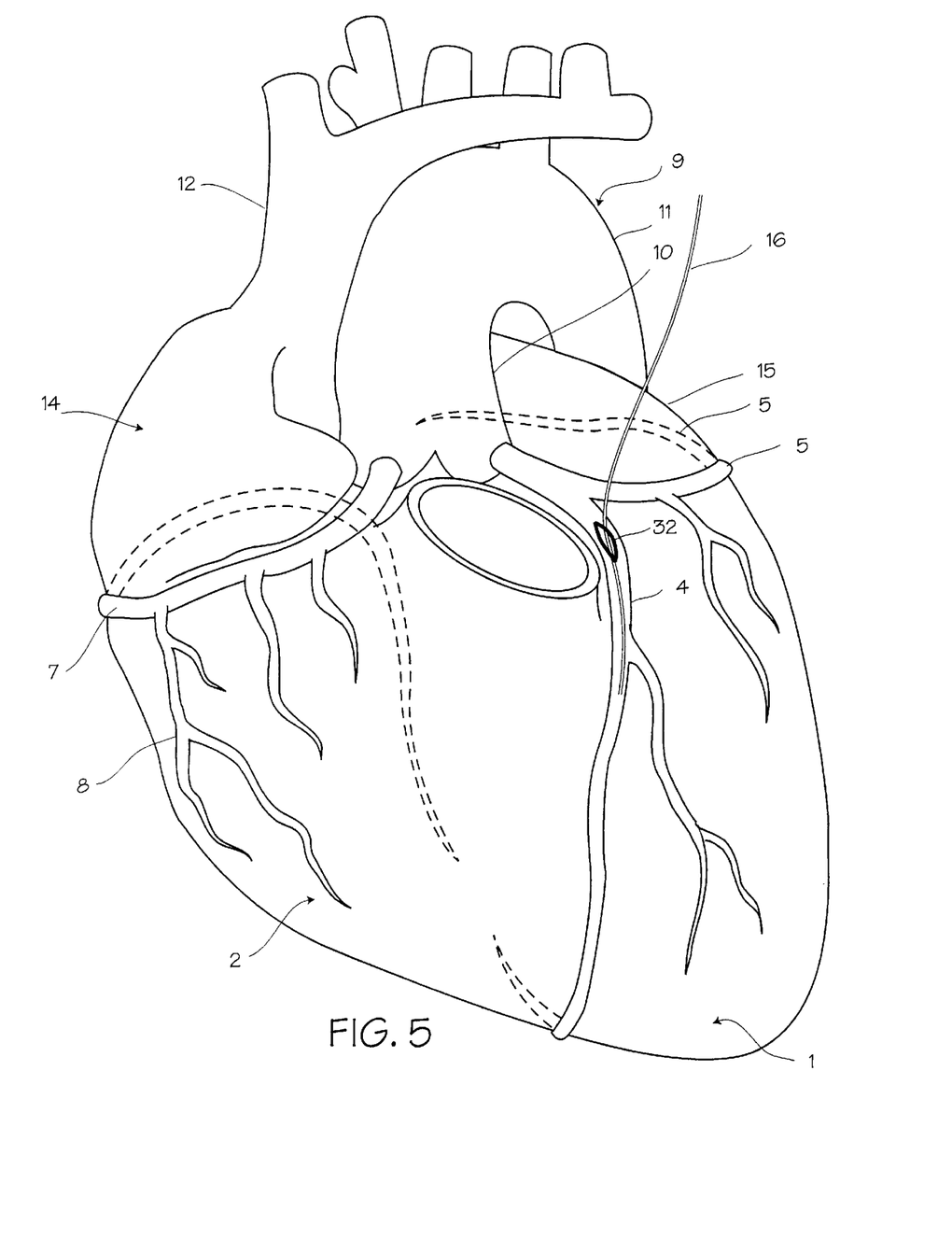
FIG. 5 is an anterior view of the heart illustrating a variation of the procedure wherein the procedure is combined with open endarterectomy.

As described in reference to FIG. 2, the channel created with the channeling catheter extends through the entire thickness of the myocardium and communicates with the left ventricle chamber. The channel may be generally perpendicular to the left ventricle wall, but is more readily made at any high angle of entry into the myocardium, and is illustrated in FIG. 2 with an angle of about 60° from the LAD. This will facilitate channeling, allow the mechanisms described below to perform in deeper and smaller coronary arteries, and lower the material requirements of the devices. Other channels angles can be used for beneficial effect. In FIG. 3, a very low angle of entry into the myocardium is used, and this results in a channel being created alongside the LAD, running parallel to the LAD. In FIG. 4, a low angle of entry and a curving channel are used to create an arterio-myocardial shunt 30 which may be maintained open with a stent or graft. The bypass around the occluded segment 31 of the LAD 4 is accomplished in a manner similar to porto-systemic shunting. As a further variant on the procedure, the devices illustrated below may be used in conjunction with a open chest endarterectomy procedure, with the channeling devices being mounted on short flexible shafts inserted into the artery through the cutdown used for the endarterectomy. This procedure is illustrated in FIG. 5, which shows a cutdown 32 in the LAD 4 with a catheter inserted into the LAD through the cutdown. This method of performing the endarterectomy is old in the art, but is still medically indicated in some circumstances. Combination of the transvascular TMR procedure with the endarterectomy provides the benefits of TMR without further disrupting the pericardium.

Figures 6, 7:
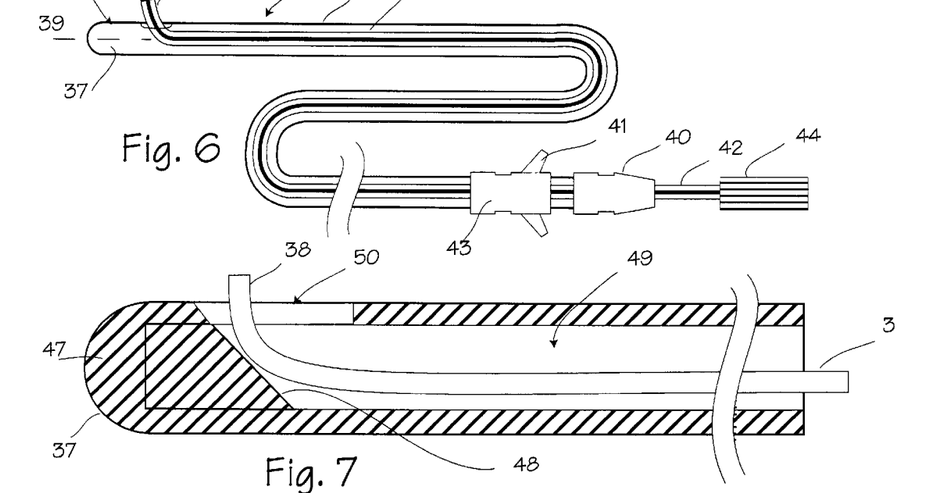
FIG. 6 shows a basic embodiment of a catheter assembly including a deflecting catheter and a channeling catheter.
FIG. 7 is a detail view of the distal tip of the deflecting catheter and channeling catheter assembly.

FIG. 6 shows a basic embodiment of a catheter assembly. The catheter assembly 33 includes a deflecting catheter 34 having a lumen running from the distal end to the proximal end, and a channeling catheter 35 disposed within the lumen of the deflecting catheter. Both the deflecting catheter and the channeling catheter bodies are flexible elongate tubular members capable of percutaneous insertion into the coronary blood vessels, and many suitable catheter materials are commercially available. The catheters will be about 100–200 cm long, preferably about 135 cm long, so that they may reach from the femoral artery access point in the thigh to the coronary arteries around the heart. The deflecting catheter has, at its distal end 36, a deflecting tip 37 which directs the distal tip 38 of the channeling catheter away from the longitudinal axis 39 of the assembly when the channeling catheter is pushed out of the lumen. The deflecting catheter has, at its proximal end, an outlet and a blood tight seal 40 for passage of the channeling catheter and/or control mechanisms for the channeling catheter. Additional lumens may be provided for flushing or aspiration of the blood vessel in which the channeling catheter will operate and the new TMR channel which it will create, and these additional lumens may be supplied with side ports 41. The channeling catheter has a means for creating channels in the heart disposed on the distal tip. The means for creating channels may be a mechanical cutting or boring assembly, an optical fiber delivering a high power laser beam, or an RF electrode delivering high power RF energy. The channeling catheter proximal end 42 may extend a convenient distance from the proximal end of the deflecting catheter for convenient handling, especially in the mechanical boring embodiments where boring is to be accomplished by forward movement of the channeling catheter itself. Electrical, optical, and/or mechanical control mechanisms may be attached to the deflecting catheter via an appropriate proximal hub 43, and may also be attached to the channeling catheter via proximal hub 44.

Figure 8:
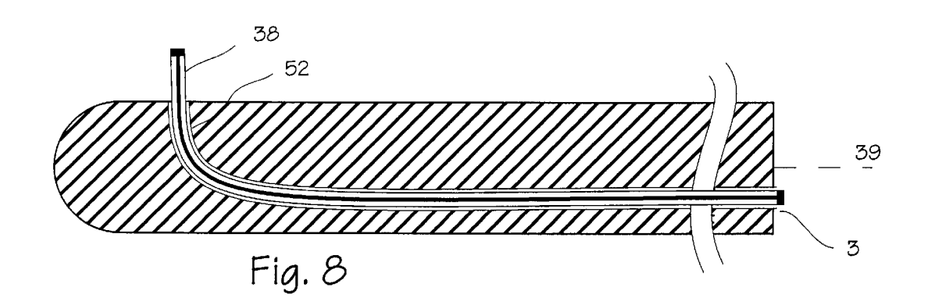
FIG. 8 is a detail view of the distal tip of the deflecting catheter and channeling catheter assembly.

FIG. 7 is a detail view of the distal tip of the deflecting catheter and channeling catheter assembly. The deflecting tip 37 of the deflecting catheter generally comprises an atraumatic bullet nosed tip 47, a deflecting surface 48 which opposes the longitudinally oriented lumen 49, and a side facing aperture 50 communicating with the lumen 49. The lumen 49 of the deflecting tip communicates with the lumen 51 of the deflecting catheter which extends the length of the deflecting catheter. FIG. 8 shows an alternative construction of the deflecting tip, wherein the deflecting surface and lumen are integrally formed to create a smoothly arcing deflecting lumen 52 which turns from the longitudinal orientation, generally in line with the longitudinal axis 39 at the junction with the deflecting catheter lumen to a radial orientation at the aperture. When channeling catheter 35 is pushed distally through the deflecting catheter, the channeling tip is directed by the deflecting tip to exit the deflecting catheter at an angle from the longitudinal axis. The degree of deflection and the angle of entry into the myocardium is determined by the angle of the deflecting surfaces. In many respects, the deflecting catheter may be assembled in accordance with our earlier patent, Fogarty, Deflecting Guide Catheter, U.S. Pat. No. 4,774,949 (Oct. 4, 1988).

Figure 9:
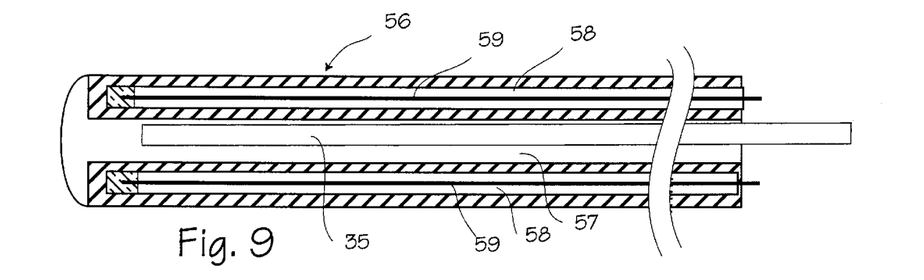
FIG. 9 is a detail view of the distal tip of the steerable catheter and channeling catheter assembly.
Figure 17:
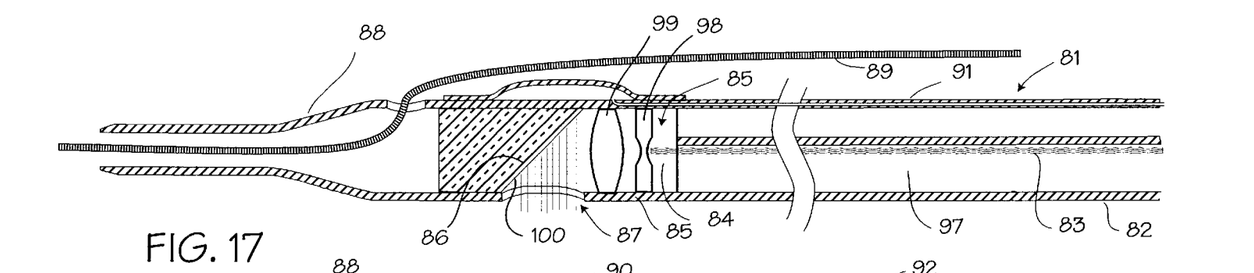
FIG. 17 is a cross section of the side-firing laser catheter.

The channeling catheter may also be directed into the myocardium at the appropriate angle by use of a steerable catheter. FIG. 9 shows a steerable catheter 56 having a central lumen 57 and side lumens 58. The channeling catheter 35 resides within the central lumen and may be advanced out of the distal tip of the steerable catheter. Pullwires 59 in the side lumens 58 extend to the proximal end of the steerable catheter and connect to appropriate control mechanisms, which may be mechanical pulling devices and lock-downs, or may be electrical current supplies where shape memory pullwires are used. Several pullwires may be used in the steerable catheter, dispersed radially around the catheter, to provide for increased control of the tip. Various other embodiments of steerable catheters, all well known in the art, may be used. It should be noted that not all embodiments of the catheter assembly will require the deflecting catheter/channeling catheter combination, and that other embodiments of the device capable of producing TMR channels from within the coronary arteries and veins maybe constructed. FIG. 17, described in detail below, represents one such embodiment wherein a side-firing laser catheter is used to produce the TMR channels.

With the various means for delivering a channeling catheter to the myocardium via the vasculature described above, the various boring mechanisms may now be discussed. In its simplest form, the boring device may be made of a stiff wire punch with a sharp tip, with sufficient column strength to be forced through the coronary artery wall and well into the myocardium. A stainless steel or nitinol hypotube may also be used to punch through the myocardium. In practice, it is believed that an initial puncture will be made with either a stiff wire or hypotube, and a coring device will be tracked over the wire or hypotube. Additionally, where puncture of the myocardium proves difficult with a stiff guidewire, the initial puncture may be made with a hypotube, followed by placement of a guidewire through the hypotube and withdrawal of the hypotube, leaving the guidewire in place for easy insertion of the coring catheter.

Figure 10:
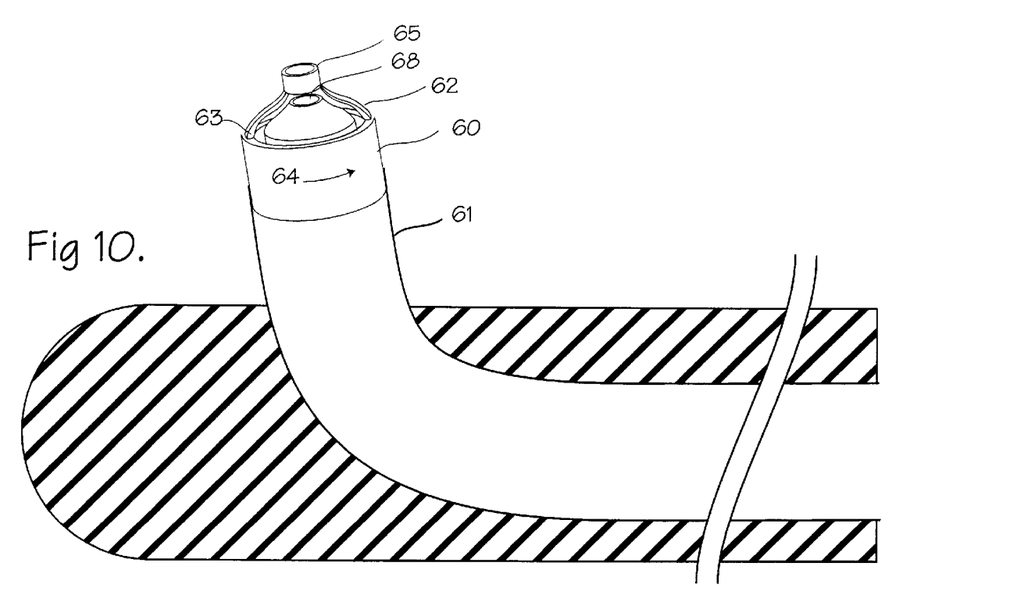
FIG. 10 is a detail view of the channeling catheter tip.
Figure 11:
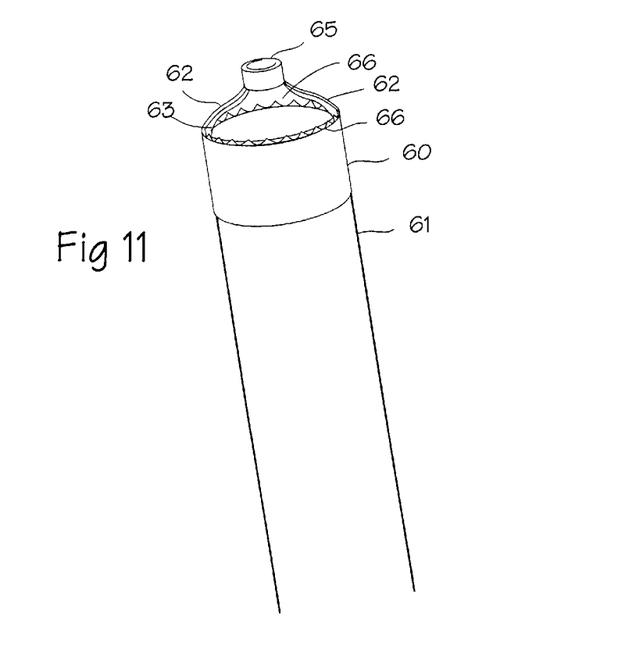
FIG. 11 shows a detail view of another embodiment of the channeling catheter tip.

FIG. 10 shows a detail view of the first preferred embodiment of the boring catheter tip. The device is similar to a hole saw or open drill bit. The bore 60 is attached to the boring catheter shaft 61 by welding, adhesives or solder. The bore supports radial cutting blade 62 which has cutting edges 63a and 63b facing the direction of rotation, indicated by arrow 64. A guidewire mounting ring 65 connects the opposing cutting blades. The guidewire mounting ring preferably has an internal diameter to fit standard coronary guidewires (sizes of 0.014, 0.016, or 0.018 inches are standard). To illustrate the typical size of the boring tip, the prototype has a guidewire mounting ring of 0.015" internal diameter and 0.025" length, a bore of 0.1" diameter and 0.060" length, and a blade thickness of 0.007" and a blade height of 0.050" which corresponds to a blade pitch of about 45°. The distal edge of the bore may be provided with a sharp edge, as shown in FIG. 10, or it may have a serrated edge 66 as illustrated in FIG. 11. Inside the boring tip is a rotating cutting core 67 with a guidewire lumen 68 in the center. The distal edge of the cutting core is sharpened, and may be slightly pitched to drive cut myocardial tissue into the lumen of the coring catheter. The cutting core is generally round in cross section, leaving space within the coring catheter to store cut myocardial tissue. The catheter may have to be removed for intra-operative cleaning or replacement, depending on the amount of myocardial tissue cored out by the coring tip and cutting core. The cutting core is rotated by means of a motor and clutch assembly, as is known in the catheter art, especially in relation to atherectomy devices and other endoscopic rotational devices.

Figure 12:
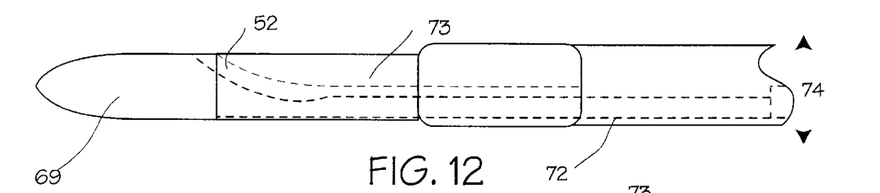
FIG. 12 is a cross section of the two-part deflecting guide catheter.
Figures 13, 14, 15, 16:
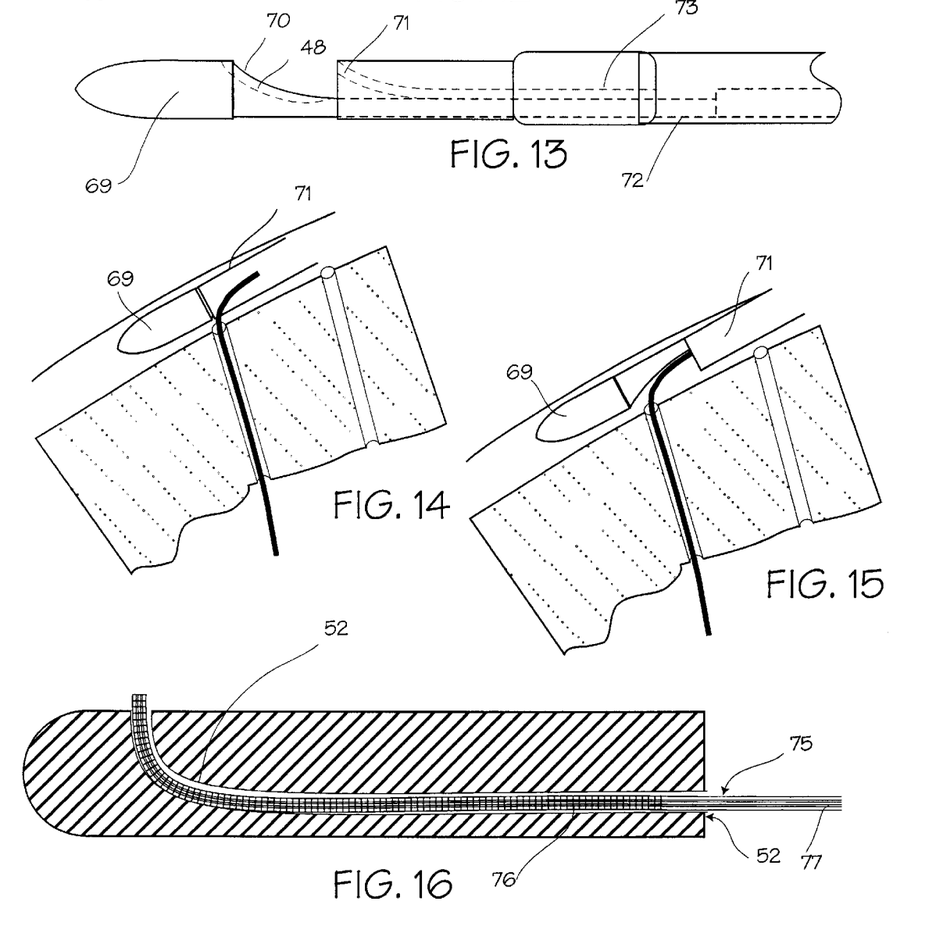
FIG. 13 is a cross section of the two-part deflecting guide catheter.
FIG. 14 is a view of the two-part deflecting guide catheter in use.
FIG. 15 is a view of the two-part deflecting guide catheter in use.
FIG. 16 is a cross section of the TMR catheter comprising a deflecting guide catheter and an end-firing laser guidewire.

The most convenient and reliable way of properly placing the coring catheter will be to first insert a stiff guidewire through the myocardium, and deliver the coring catheter over the guidewire. Design requirements for the coring catheter are less demanding, in terms of size and flexibility, if the deflecting catheter is removed before insertion of the coring catheter. The coring catheter will track over the guidewire which, when properly punched through the myocardium, will ensure that the channel created with the coring channel follows the path of the guidewire through the myocardium. For this variation of the procedure, the deflecting catheter may be modified as shown in FIGS. 12 & 13. The separable distal tip 69 of deflecting catheter, which constitutes the deflecting surface 48, is longitudinally separable from the remainder of the deflecting catheter. The deflecting tip includes the back half 70 of the deflecting channel 52, while the remaining portion of the catheter constitutes the guiding cover 71 of the deflecting channel 52. The deflecting tip is integrally formed with and connected to a longitudinally slidable member 72 of the catheter. The guiding cover 71 is connected to and integrally formed with a main lumen 73 of the catheter. This portion of the catheter serves to cover the deflecting channel and guide and trap the guidewire or other device within the deflecting lumen. When the two halves are held in place together, they form the deflecting catheter with a side facing aperture. When the deflecting tip portion and covering portion of the catheter are separated as illustrated in FIG. 13, the guidewire is released from the closely fitting deflecting catheter. The covering portion and deflecting portion may be withdrawn one at a time without pulling the guidewire backward along with the deflecting catheter. The two halves of the deflecting catheter can also be constructed as two radial segments of a catheter defining a lumen between the segments, longitudinally movable relative to each other.

In use, as illustrated in FIG. 14, a guidewire will be pushed through the lumen and will be deflected by the curving deflecting channel to exit out the side of the catheter. After leaving the catheter, the guidewire will enter the myocardium, and will be pushed completely through the myocardium. With the guidewire in place, the covering portion 71 will be pulled back to open the deflecting channel, as depicted in FIG. 15. Withdrawal of the covering portion releases the guidewire from the deflecting lumen. If desired, the separable deflecting tip 69 and cover 71 may also be withdrawn before the boring catheter is placed over the guidewire. With the catheter now in two parts, the guidewire lumen will not tightly grasp the guidewire, and withdrawal of the deflecting tip does not threaten to dislodge the guidewire. In a variation of the procedure, the deflecting tip may be left in place while the boring catheter is tracked along the guidewire, so that it will be in place and ready for use in creating another TMR channel. The outer diameter 74 of the catheter may be as large as the target coronary blood vessel, about 4–5 mm in diameter, and the inner diameter of the guidewire lumen should approximate standard guidewire sizes (currently 0.014, 0.016, or 0.018 inches are standard diameters for coronary guidewires).

The above description provides devices for accomplishing the transvascular TMR procedure with mechanical boring. Lasers, which are used for exterior TMR and proposed for endocardial ablation procedures, can be modified for use in the transvascular TMR procedure. Because the lasers may be side-firing lasers, the design of the delivery catheter is facilitated. However, various design modifications must be made to the lens and optics used to deliver laser power to the myocardium to create a clean and narrow channel. Side-firing and end-firing lasers in the prior art are essentially contact devices, meaning that they vaporize only a small amount of tissue directly in front of the lens. If it is desired to lase a deep channel, that laser lens must be pushed into the myocardium as it lases the myocardial tissue in contact with the lens. This is illustrated by Aita, U.S. Pat. No. 5,380,316. Such a laser assembly as described in Aita, may be mounted on a catheter and the resulting assembly may used as the channeling catheter delivered through the deflecting guide catheter as described above. It may be delivered through the deflecting guide catheter with or without the assistance of the guidewire, or it may be tracked over the guidewire after withdrawal of the deflecting guidewire, as described in reference to the mechanical boring catheter. FIG. 16 illustrates the use of an end-firing laser in the deflecting catheter. The end firing laser catheter or laser guidewire 75 resides in the deflecting lumen 52. Support coil 76 provides columnar support for the laser guidewire tip while it is being advanced through the myocardium. Optical fibers 77 are bundled in the center of the laser catheter. The laser energy is directed distally from the end of the optical fibers. A suitable laser guidewire of 0.018 in. diameter is available from Spectranetics Corporation of Colorado Springs, Colorado. The Spectranetics laser guidewire is designed for use in lasing through occlusions in the coronary arteries, but in combination with the deflecting guidewire it is well suited for use in transvascular TMR. It may be modified by provision of a stiffer distal tip to better enable lateral passage through the myocardium. Larger diameter end firing lasers may also be used, and diameters are limited only by the space available in the coronary arteries and limits imposed by the required deflection of the catheter.

An alternative to the end-firing laser is the side firing laser illustrated in FIG. 17. The laser catheter 81 includes the catheter body 82 and an optical fiber 83 running from the proximal end of the catheter body to the distal end of the catheter body, where its optical outlet 84, which is the flat distal end of the optical fiber, directs light to lens assembly 85. The mirror 86 opposes the lens assembly and is angled to direct laser light sideways, out the optical window 87. The optical window 87 may be a cutout in the side wall of the catheter, or it may be a transparent fill material. The catheter may be provided with a rapid exchange tip 88 which accommodates a guidewire 89 to be used to guide the laser catheter into place in the coronary blood vessels.

The optical fiber 83 is preferably a fused silica fiber with a core diameter of between 50 and 200 microns, and a numerical aperture in the range of 0.12 to 0.26. Numerical aperture, which is defined as the sine of the angle between a ray of light and the optical axis multiplied by the refractive index of the medium in which the light travels, can be thought of as an indicator of the divergence of the light beam as it exits the optical fiber. Numerical aperture, beam spreading, and loss of beam intensity are related physical characteristics of the laser beam that are preferably limited in order to provide a deep penetrating laser beam which can lase a narrow channel through the entire myocardium. If, for example, a fiber of 100 micron diameter with a 0.26 numerical aperture is used, the light emitted from the fiber can be up-collimated. In collimating the light beam, the numerical aperture is reduced by a factor equivalent to the increase in the beam diameter. Thus, for a 100 micron fiber emitting a 100 micron collimated beam of light which is enlarged by the lens assembly to a 1 mm beam (equal to 1000 microns), the effective numerical aperture will be 0.026. This means that the laser beam leaving the lens assembly will diverge 0.26 mm for every centimeter it travels. Typically, channels up to 2 cm in length may be created through the myocardium, so the laser beam will diverge only about 0.52 mm as it channels through the myocardium. This small divergence will provide a beam of sufficient power to lase all the way through the myocardium without using an extremely powerful laser beam that must burn a wide hole into the myocardium. The side firing, free-beam, non-divergent laser catheter created by the lens assembly permits creation of the channels in the myocardium in the shape desired for forming shunts between the left ventricle and the coronary arteries and veins.

Figure 18:
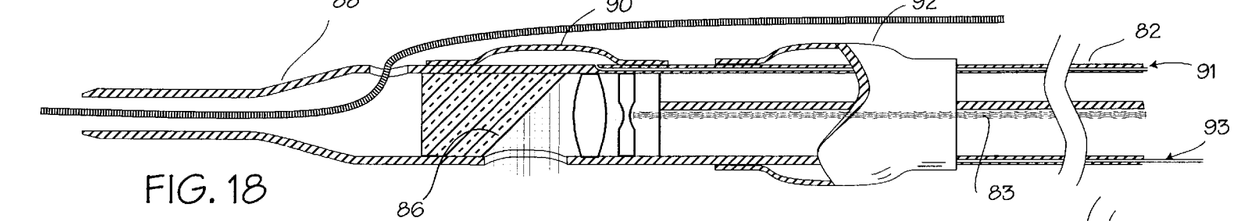
FIG. 18 is a cross section of the side-firing laser catheter.
Figures 19, 20:
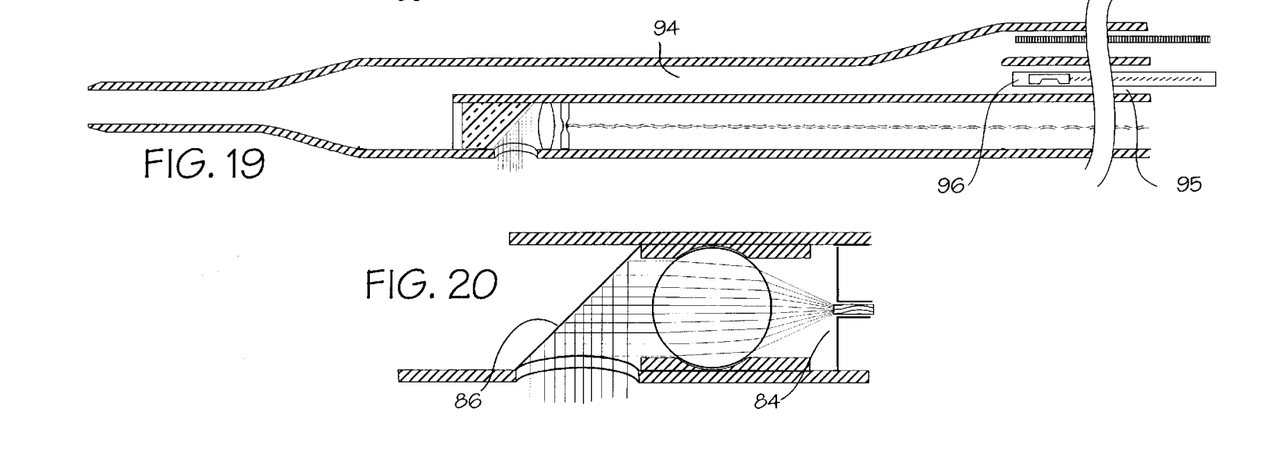
FIG. 19 is a detail view of the lens assembly used in the side-firing laser.
FIG. 20 is a detail view of the lens assembly used in the side-firing laser.

To improve the function of the laser catheter, various constructions of the catheter may be used to limit the amount of blood which flows between the laser optical window and the side wall of the blood vessel. In one such construction, the laser may be applied to the coronary blood vessel and myocardium in a contacting relationship, and a balloon 90 may be applied to the catheter radially opposite the optical window as shown in FIGS. 17 & 18. This balloon may be inflated to press the optical window into direct contact with the blood vessel. Inflation lumen 91 extends to the proximal end of the catheter and can be supplied with an inflation fluid such as saline solution. Another embodiment in shown in FIG. 18, which shows a proximal occluding balloon 92 located proximal of the optical window and the balloon 90 located radially opposite of the optical window. An inflation fluid lumen is provided for each balloon, or a single lumen may be used for both lumens. A flushing fluid lumen 93 communicates with the exterior of the catheter in the vicinity of the optical window. In use, the proximal balloon is inflated to occlude the blood vessel, saline solution is pumped through the flushing lumen to flush blood into the occluded space distal to the proximal balloon. The side balloon 90 may be inflated to push the optical window into contact with the blood vessel wall. A distal balloon (not shown) may be used to completely isolate the optical window from the blood vessel so that the flushing lumen may be used to fill the occluded space between the balloons with clear saline solution. FIG. 19 shows another embodiment of the catheter which includes low profile guidewire lumen 94 and ultrasound lumen 95. An intravascular ultrasound probe 96 provides visualization of the blood vessel walls and the myocardium, and allows the surgeon operating the laser catheter to ensure that the optical window is facing the myocardium during the channeling operation.

Alternatively, A-mode ultrasound may be used to orient the catheter. This may be accomplished by mounting at least one ultrasound transducer on the catheter such that the ultrasound wave is oriented primarily in the direction that the side firing laser is pointed. The reflectance peaks, and more specifically the distance between the reflectance peaks, will indicated when the catheter is pointed in the correct direction. The distance between the reflectance peaks, as measured in time on a scope or monitor, corresponds to the distance between the tissue interfaces, such as the interface between the blood vessel and the heart muscle, and the interface between the myocardium and the intraventricular space, and also the interface between the blood vessel and the pericardial space, and the pericardium and the sternum. When the peaks are very close together, it generally will indicate that the catheter is pointed away from the myocardium, and the peaks will indicate relative position of the wall of the coronary artery, the pericardium, and the structures beyond the pericardium as penetration of the ultrasound signal allows. As the distance between the peaks grows, it will indicate that the catheter is facing the myocardium. If it is desired to create a channel that communicates with the intraventricular space, the catheter must be rotated until the reflectance peaks are at some minimum relative distance apart. If the catheter faces directly into the septum, the peaks will be widely separated, and if the catheter were rotated such that the side aperture nears the left ventricular aspect of the artery, the peaks would be seen to get closer together, as the section of myocardium that the ultrasound beam traverses would grow shorter, to some relative minimum value, whereafter the myocardium that the beam must traverse would again grow thicker and the peaks would become farther apart as the optical window of catheter is rotated further away from the myocardium.

The laser beam is supplied by an excimer laser with a wavelength of 308 nm. Spectranetics, Inc. and various other laser manufacturers supply suitable lasers. Laser power of approximately 30–60 $mJ/mm^2$ has been successfully used to lase narrow 1 mm through channels myocardial tissue of 2–3 cm thickness. $CO_2$ lasers, which are also commercially available for medical use, may also be used. The lens assembly 85 is shown in detail in FIGS. 17 through 19. The lens assembly 85 is disposed inside catheter 81, retained between the catheter walls 82. The lens assembly is located just proximal of the optical window 87. The optical fiber 83 is held within a lumen 97 (any other means of support may be used). The optical fiber output 84 directs the collimated laser beam into the concave lens 98, located and fixed between the catheter walls 82 in position immediately distal to the optical output. A convex lens 99 is located immediately distal to the concave lens, and immediately before the optical window 87. This arrangement is a simple example of a telescope lens assembly. The mirror surface 100 is beveled over the optical window to reflect collimated light laterally, at an angle to the long axis of the catheter. The angle of reflection may be varied by varying the angle of the mirror. The lenses serve to broaden the laser beam from the initial diameter of 100 microns to about 1 mm (for example), while regaining the collimation and minimizing beam divergence. This means that the lenses serve to up-collimate the beam, thereby reducing the divergence of the beam. In this manner, the laser and lens assembly provide a laser beam which exits the optical window with sufficient power and tight collimation for lasing deep channels into the myocardium. FIG. 20 shows an alternate lens assembly which is made of a spherical lens mounted between the optical fiber outlet 84 and the laser mirror 86.

Figure 21:
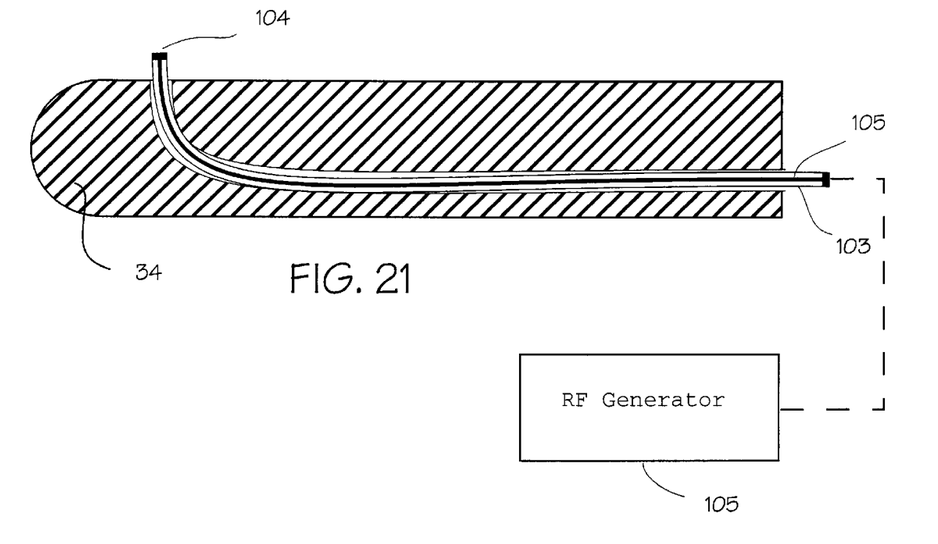
FIG. 21 is a cross section of the TMR catheter comprising a deflecting guide catheter and an RF catheter.

Another mechanism for creating channels through the myocardium is an RF (radiofrequency) catheter. RF ablation catheters have been used for endocardial ablation for the control of arrhythmias and for endovascular ablation of stenotic lesions. RF electrocautery tools have also been used for cutting through various body tissues. For use as a TMR catheter, an RF electrode is mounted on the distal tip of a small diameter RF catheter 103 inside the deflecting catheter 34, as shown in FIG. 21. The RF electrode 104 is electrically connected to an RF generator 105 through the electrical wire 106. Suitable RF generators are commercially available, such as the Surgitron® supplied by Elman, Inc. The electrode tip diameter of 0.25–1 mm will produce a narrow channel of about 0.4–2 mm through the myocardium. Numerous suitable RF power sources are commercially available. The electrode may be operated in a monopolar mode, in which case a patch electrode will be placed on the skin of patient to complete the electrical pathway required for the RF electrode. The catheter may also be provided with bipolar capability by placing a ground electrode in close proximity to the RF electrode on the RF catheter or on the deflecting catheter. In use, the RF channeling catheter will be advanced from the deflecting catheter until it makes contact with the blood vessel wall. When contact is established the RF energy will be supplied to the electrode at power levels high enough to tunnel through the blood vessel wall, and the electrode tip will be pushed from the proximal end to force it through the blood vessel wall and through the myocardium. Balloons similar to those shown in FIG. 18, used there to isolate and stabilize the catheter, may be used in combination with the RF channeling catheter and deflecting catheter to press the catheter into contact with the blood vessel wall and achieve and maintain the proper direction for the deflecting catheter aperture.

The description of the overall device provided above is sufficient to enable creation of TMR channels via the coronary vasculature. Many channeling catheters may be used to create the channels. Various means for creating channels in the myocardium, either mechanically, with lasers or with RF energy, have been described, but many other embodiments of channeling instruments may be devised and used in devices which incorporate the inventions described above. While the inventors have exemplified their invention in the form of the deflecting/steering catheter and channeling catheter combination, the two functions of deflecting/steering the catheter and creating the channels may be combined in a single catheter fitted with both deflecting/steering means and a channel means. One such example is the side firing laser of FIG. 18. Another such example could be devised by incorporating pullwire steering mechanisms into the walls of the laser guidewire described in reference to FIG. 16.

The inventors have devised several embodiments that permit easy creation of channels of the appropriate diameter, without undue damage to surrounding tissue. After the channels are created, they may be treated with other intraluminal therapies to enhance patency. Balloon angioplasty may be performed on the TMR channels. Stents, stent grafts, or autologous vein grafts may be placed in the TMR channels to physically hold them open for an extended period of time. Growth factors or drugs may be infused directly onto or into the wall of the newly created channel in order to maintain patency or to stimulate the growth of new blood vessels nearby.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for making channels in heart, said device comprising:

a means for channeling throuah the heart; and a means for delivering said means for channeling to the heart through the coronary blood vessels, wherein the means for channeling through the heart comprises an RF catheter having an RF electrode disposed on the distal tip of said RF catheter and an RF generator operably connected to said RF electrode.

2. A device for making channels in heart from the coronary blood vessels of a patient, said device comprising:

an RF catheter having an RF electrode disposed on the distal tip of said RF catheter and an RF generator operably connected to said RF electrode; and said RF catheter being housed within a deflecting catheter, said deflecting catheter having a lumen extending from the proximal end of the deflecting catheter to the distal end of the deflecting catheter and terminating near the distal end of the deflecting catheter in a side facing aperture, said RF catheter being slidably disposed with the lumen;

wherein the distal end of said deflecting catheter is sized and dimensioned to be inserted into the coronary blood vessels of the patient, and the side facing aperture is positioned on the deflecting catheter so that it communicates with the coronary blood vessel when the distal end of the deflecting catheter is inserted into the coronary blood vessel.

* * * * *